United States Patent [19]
Turkel et al.

[11] Patent Number: 5,395,375
[45] Date of Patent: Mar. 7, 1995

[54] ARTHROSCOPIC SURGICAL INSTRUMENTS

[75] Inventors: David Turkel, Miami; Kevin Hahnen, Ft. Lauderdale, both of Fla.

[73] Assignee: Symbiosis Corporation, Miami, Fla.

[21] Appl. No.: 978,249

[22] Filed: Nov. 18, 1992

[51] Int. Cl.⁶ ............... A61B 17/56; A61B 17/32
[52] U.S. Cl. .................... 606/83; 606/174
[58] Field of Search ............ 606/79, 83, 167, 174, 606/175, 175, 184, 207, 208; 188/376; 128/751; 604/22

[56] References Cited
U.S. PATENT DOCUMENTS

| | | | |
|---|---|---|---|
| 1,754,806 | 4/1930 | Stevenson | 606/174 |
| 3,504,460 | 4/1970 | Solberg | 188/376 |
| 4,522,206 | 6/1985 | Whipple et al. | 606/174 |
| 4,712,545 | 12/1987 | Honkanen | 128/751 |
| 4,896,678 | 1/1990 | Ogawa | 128/751 |
| 4,994,024 | 2/1991 | Falk | 606/83 |
| 5,219,357 | 6/1993 | Honkanen et al. | 606/174 |

*Primary Examiner*—Tamara L. Graysay
*Attorney, Agent, or Firm*—David P. Gordon

[57] ABSTRACT

A disposable arthroscopic surgical instrument includes a hollow tube with a manual actuator coupled to its proximal end and an end effector coupled to its distal end. The actuator and the end effector are coupled by a push rod which passes through the hollow tube and the push rod includes a frangible link so that the push rod will break when a predetermined force is applied to the end effector by the actuator. The frangible link is a flattened portion of the cylindrical push rod having a strength reducing throughbore. An end effector having a stationary jaw and a movable jaw is also disclosed. The stationary jaw is coupled to the distal end of the tube and has a throughbore for receiving the push rod. The movable jaw is coupled to push rod and is pivotally coupled to the stationary jaw by arcuate engaging surfaces on both jaws. The movable jaw preferably includes a pair of arcuate grooves while the stationary jaw has a pair of arcuate flanges which engage the grooves on the movable jaw. The movable jaw is also provided with a knife-like edge and the stationary jaw is provided with a receiving opening into which the movable jaw fits when the jaws are in a closed position.

20 Claims, 3 Drawing Sheets

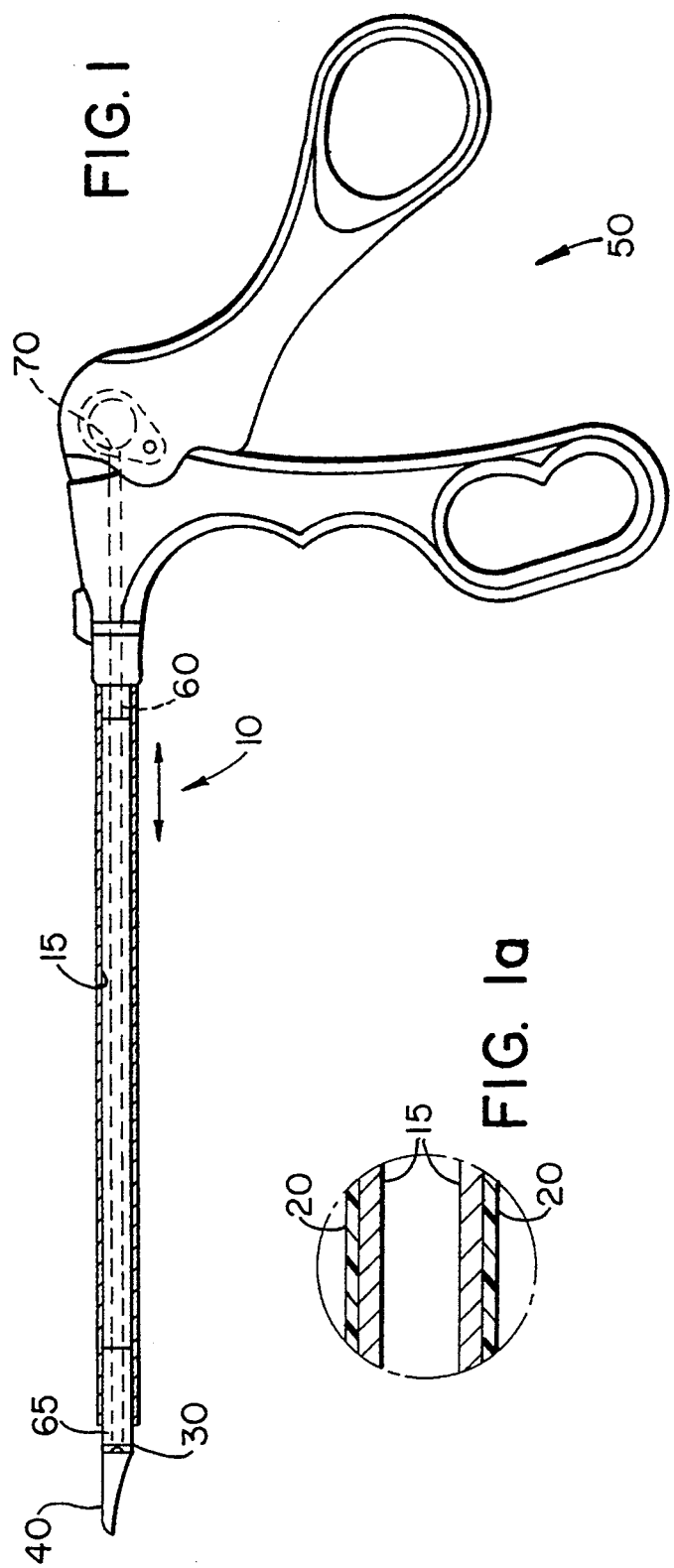
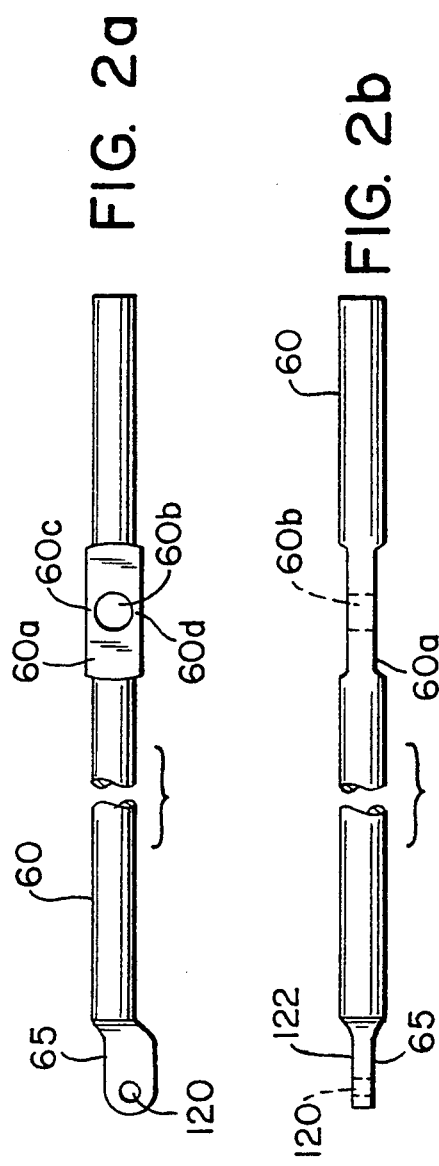

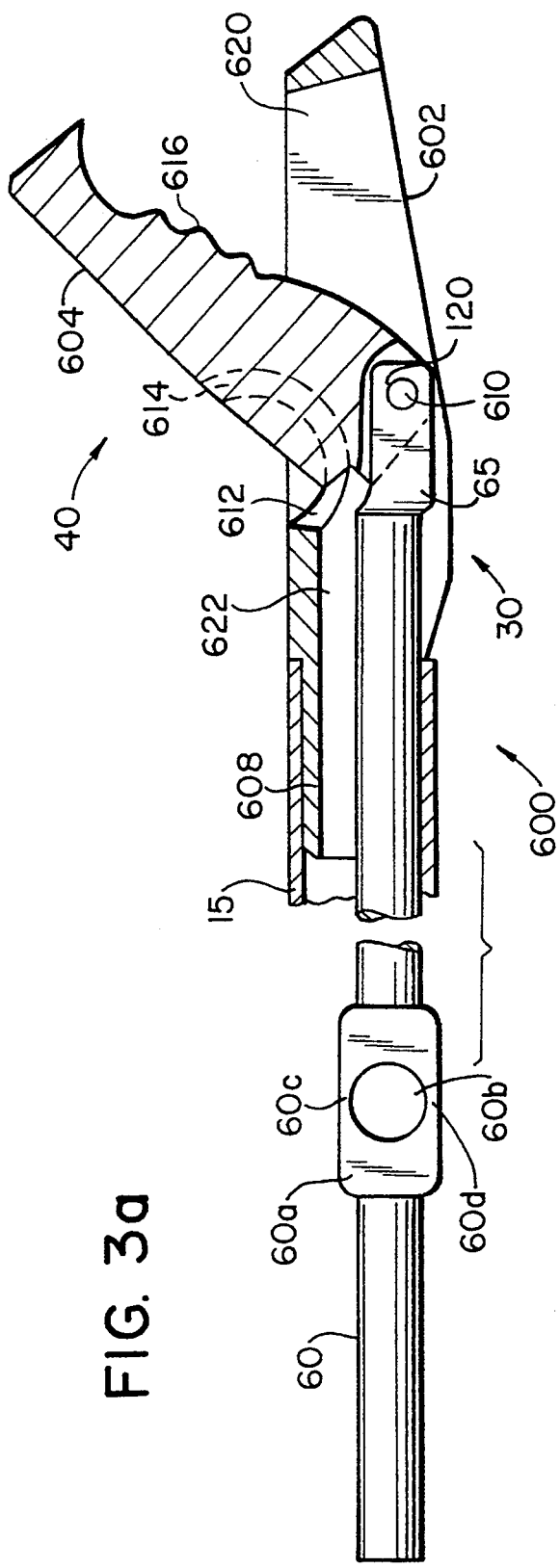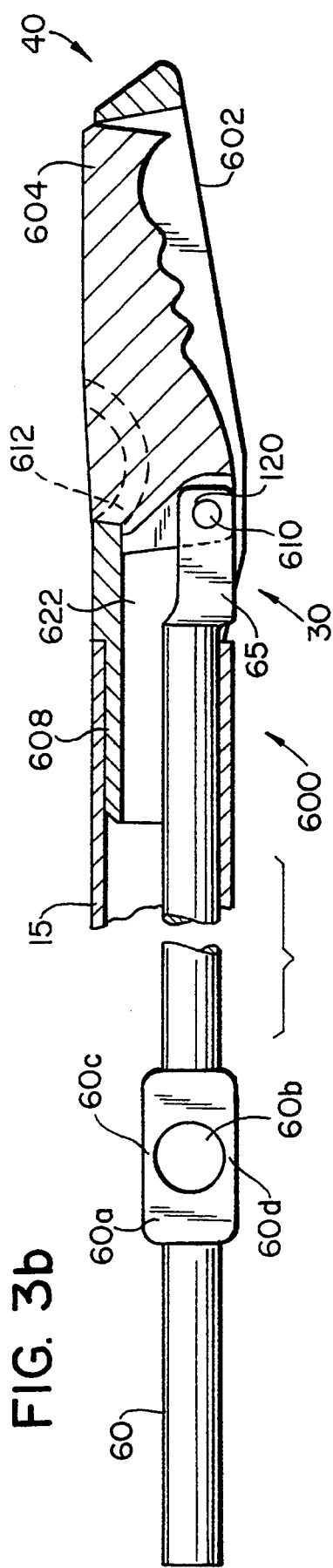
FIG. 3a
FIG. 3b

ARTHROSCOPIC SURGICAL INSTRUMENTS

BACKGROUND OF THE INVENTION

The present invention broadly relates to arthroscopic surgical instruments. More particularly, the invention relates to arthroscopic surgical instruments which are preferably disposable and which include push rods with a failure mechanism for excess force, and end effectors with desired arrangements.

The arthroscopy procedure has become a widely practiced surgical procedure. Arthroscopy involves making one or more relatively small incisions in order to examine the interior of a joint with an endoscope and to perform surgical operations on the joint. Typically, the surgical procedure involves inserting a cutter, dissector, or other surgical instrument through the incision for purposes of manipulating and/or cutting the bone and cartilage comprising the joint.

The disposable arthroscopic tools of the prior art are somewhat similar to other endoscopic tools used in endoscopic procedures involving softer tissues and organs. These tools, such as laparoscopy tools, generally include a tube, a push rod which extends through the tube, an actuating means engaging the tube and the push rod for imparting reciprocal axial motion to the push rod, end effector means coupled to the push rod, and a clevis coupled to the tube at its proximal end and to the end effector means at its distal end, wherein axial movement of the push rod effects movement of the end effector means in a plane parallel to the longitudinal axis of the push rod. The end effector means of the art can take any of many forms, such as, e.g., a scissors, a dissector, or a grasper. Additionally, the end effector means can be double acting or single acting.

Since there is a limit as to how strong the tools of the art can be made and still be small enough for use in arthroscopy, there is always the possibility that the tool will break while in use. Indeed, this problem is compounded with disposable tools, typically made from weaker materials than the standard stainless steel of non-disposable tools. While this is a remote possibility in most endoscopic procedures involving soft or relatively soft tissues, when used in arthroscopic procedures involving bone tissue, the possibility that an end effector or distal linkage member will break is increased since additional force must be applied to the end effectors through the actuating means in order to grasp or cut the bone tissue. In such a case, if a portion of the end effector or distal linkage breaks, it may become lodged in the joint and will require additional procedures to remove it.

In the field of endoscopy, U.S. Pat. No. 4,896,678 to Ogawa partially addresses this problem. In Ogawa, means are provided for releasing the transmission of force to the end effectors when the operating force exceeds a predetermined amount. One mechanism used by Ogawa to release the force is a V-shaped notch in the push rod which is intended to fail upon the application of excessive force. The teachings of Ogawa, however, have not been applied to arthroscopic instruments in the past.

Improvements have been made in end effectors for use in arthroscopy. In particular, durable surgical forceps and punch end effectors are disclosed in U.S. Pat. No. 4,712,545 to Honkanen. Honkanen's end effectors comprise a stationary jaw and a movable jaw wherein the movable jaw is attached to the stationary jaw by a first arcuate lug and groove arrangement and to a push rod by a second arcuate lug and groove arrangement. The push rod moves relative to the stationary jaw and engages the movable jaw by the second lug and groove arrangement so that the movable jaw is forced to slide by the first lug and groove arrangement relative to the stationary jaw to open or close. The jaws are configured in different ways to act as a punch or a forceps. This arrangement relieves much of the stress associated with the pivot point on end effectors, but is a relatively complex construction, particularly with regard to the second arcuate lug and groove arrangement.

SUMMARY OF THE INVENTION

It is therefore an object of the invention to provide an arthroscopic tool having an actuating means, a push rod and distal linkage connected to an end effector wherein the end effector and the distal linkage are protected from breakage while the tool is in use.

It is another object of the invention to provide a disposable arthroscopic tool with a force limiting push rod which may be used with a plurality of different types of end effectors.

It is also an object of the invention to provide an end effector particularly suited for arthroscopy which is particularly durable and able to withstand significant stress.

In accord with these objects which will be discussed in detail below, the arthroscopic tool of the present invention includes a tube, a push rod which extends through the tube, an actuating means engaging the tube and the push rod for imparting reciprocal axial motion to the push rod, end effector means coupled to the tube and coupled to the push rod by linkage means, wherein axial movement of the push rod effects movement of the end effector means in a plane parallel to the longitudinal axis of the push rod. The tube is preferably made of stainless steel or aluminum, the actuating means is preferably made of plastic (such as fiber filled polysulfone), the push rod is preferably made of stainless steel, and the end effector means is preferably made of an investment cast cobalt alloy or bronze. With the provided materials, the arthroscopic tool of the present invention is autoclavable, although because of the provided design which limits cost of manufacture, it may also be used as a disposable device. The end effector means can take any of many forms, such as, e.g., a scissors, a dissector, a punch, or a grasper. Additionally, the end effector means can be double acting or single acting. In order to prevent breakage of the end effector and/or the distal linkage while the tool is in use, a frangible link is provided in the push rod such that the push rod will break under a force less than the force necessary to break the end effector and/or the distal linkage. The push rod and frangible link are preferably made of stainless steel age hardened to a predetermined tensile strength.

Preferred aspects of the invention include fabricating the push rod with frangible link as a single member, forming the frangible link as a flattened piece within a cylindrical push rod, and providing the frangible link with a strength reducing throughbore. Preferred aspects of the end effector include a stationary jaw and a movable jaw coupled by a flange and groove arrangement, the stationary jaw being fixed to the tube and the movable jaw being pivotally coupled to the push rod.

Additional objects and advantages of the invention will become apparent to those skilled in the art upon reference to the detailed description taken in conjunction with the provided figures.

BRIEF DESCRIPTION OF THE DRAWINGS

FIG. 1 is a side elevation view, partly in section, of a disposable arthroscopic instrument;

FIG. 1a is a detail of a portion of the instrument shown in FIG. 1;

FIG. 2a is a side elevation view of the push rod which includes the frangible link of the invention;

FIG. 2b is a top view of the push rod of FIG. 2a;

FIG. 2c is a front elevation view of the distal end of the push rod of FIG. 2a;

FIG. 3a is a side elevation in partial cross section of a single acting surgical punch in the open position;

FIG. 3b is a view similar to FIG. 3a, but with the punch in the closed position;

DETAILED DESCRIPTION OF THE PREFERRED EMBODIMENT

Figure 4A:
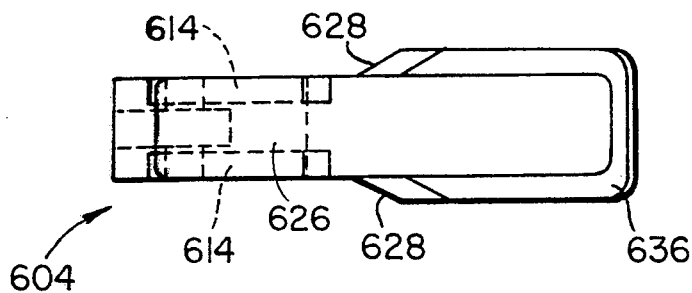
FIG. 4a is a top view of the movable jaw of the punch of FIG. 3.

With reference to FIGS. 1 and 1a, a disposable arthroscopic surgical instrument is indicated at 10. The disposable arthroscopic surgical instrument 10 broadly comprises an aluminum or stainless steel tube 15, end effectors 40, actuating means 50, and a push rod 60. If desired, the tube 15 may be surrounded by a peripheral insulating shrink wrap layer of plastic 20. The end effectors 40 are preferably formed of an investment cast cobalt alloy or bronze as disclosed in copending U.S. patent Ser. Nos. 07/837,046, and 07/780,034 which are incorporated by reference herein. The push rod 60, which in this instrument is formed of stainless steel, is engaged at its distal end 65 to the end effectors 40 through linkage 30, as more fully described below, and is connected at 70, at its proximal end to a manually operable actuating means 50. For purposes herein, the "distal end" of the instrument 10 or any part thereof, is the end closest to the surgical site and distant from the surgeon, while the "proximal end" of the instrument 10 or any part thereof, is the end most proximate the surgeon and distant the surgical site.

In use, the arthroscopy instrument 10 is inserted into a joint and the actuating means 50 are operated to impart reciprocal motion to the push rod 60. This motion of the push rod 60 is translated to movement of the end effectors 40 as described more fully below.

FIGS. 2a, 2b, and 2c show a preferred embodiment of push rod 60 for use with the arthroscopic surgical instrument according to the invention. The distal end 65 of the cylindrical push rod is provided with a flattened plate like terminal portion 122 which may be swaged from the longitudinal axis of push rod 60 as shown in FIGS. 2a and 2c. This terminal portion 122 is also provided with one or more through holes 120 for engaging an end effector as described in more detail below. In accord with the invention, push rod 60 is further provided with a weakened frangible portion 60a which, as shown in FIGS. 2a and 2b, is a flattened plate-like portion with a throughbore 60b. Throughbore 60b is dimensioned so that continuity of push rod 60 depends on small tangential link portions 60c and 60d. It will be appreciated that the strength and thus frangibility of portions 60c and 60d of push rod 60 can be specifically adjusted according to the thickness of flattened portion 60a and the diameter of throughbore 60b. In accord with the invention, these frangible link portions should have a tensile strength such that they will break before an end effector or distal linkage breaks. In furtherance of this object, the push rod 60 is ideally constructed of Carpenter Technologies Custom 455 stainless steel solution treated to an ultimate tensile strength of $-120,000/140,000$ psi with a hardness of RC 24-31. The push rod is then age hardened at 900 degrees F. for one hour and air cooled in a protective atmosphere to an ultimate tensile strength of $-250,000/290,000$ psi with a hardness of RC 44-50. The diameter of push rod 60 is typically $.061\pm.001$ inches. Flattened frangible portion 60a will have a typical thickness of $.030\pm.002$ inches and a height of $.1\pm.005$ inches thereby extending slightly beyond the diameter of push rod 60. Through hole has a typical diameter of $.076\pm.001$ inches. The flattened plate like terminal portion 122 of distal end 65 of the push rod 60 typically has a thickness of $.030\pm.002$ inches, a height of $.065\pm.005$ inches and is offset from the longitudinal axis of the push rod by $.019\pm.0015$ inches. The through hole 120 typically has a diameter of $.031\pm.001$ inches and is centered $.030\pm.002$ inches from the distal end of portion 122. With the provided dimensions and materials, the push rod has a tensile strength of approximately one hundred and ten pounds.

FIGS. 3a and 3b show a surgical punch end effector 600 particularly suited for arthroscopy. The end effector 600 comprises a stationary jaw 602 and a movable jaw 604. The stationary jaw has a, shank portion 608 which fits lockingly inside tube 15 and which is provided with a throughbore 622 for receiving push rod 60. The movable jaw 604 is pivotally attached to stationary jaw 602 by mating surfaces 612, 614, described more fully below and is linked to the distal end 65 of push rod 60 by a pin 610. The stationary jaw is provided with an opening 620 (shown in more detail in FIGS. 5a and 5b) into which the movable jaw pivots as shown in FIG. 3b. In this way, the stationary jaw 602 functions as a die and the movable jaw 604 functions as a punch for cutting through bone tissue. To further this function, movable jaw 604 is provided with a knife-like edge 616. Movement of the push rod 60 causes movable jaw 604 to pivot relative to stationary jaw 602 to an open position as shown in FIG. 3a or a closed position as shown in FIG. 3b.

Figure 4B:
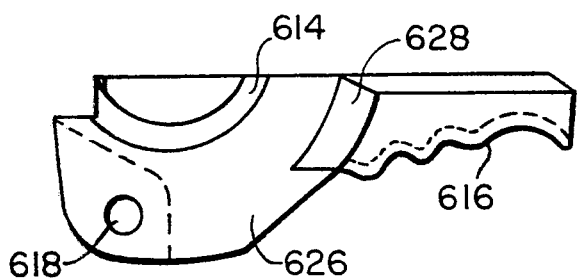
FIG. 4b is a side view of the movable jaw of the punch of FIG. 3.

FIGS. 4 and 5 show further details of the jaws 602, 604 of the arthroscopic punch end effector. Referring now to FIGS. 4a and 4b, the movable jaw 604 has a shank portion 626 and a head portion 636. The shank portion is somewhat narrower and includes arcuate grooves 614, for mating with arcuate flanges 612 of the stationary jaw 602 and a throughbore 618 for receiving push rod pin 610 (FIGS. 3a and 3b). The head portion 636 is somewhat broader than the shank portion but small enough to fit inside opening 620 of stationary jaw 602. The head portion is provided with a knife-like edge 616 and is joined to the shank portion 626 by tapered shoulders 628.

Figure 5A:
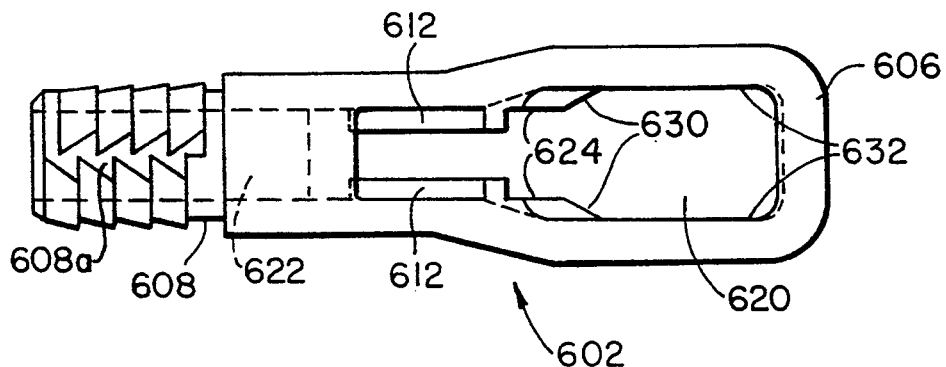
FIG. 5a is a top view of the stationary jaw of the punch of FIG. 3.
Figure 5B:
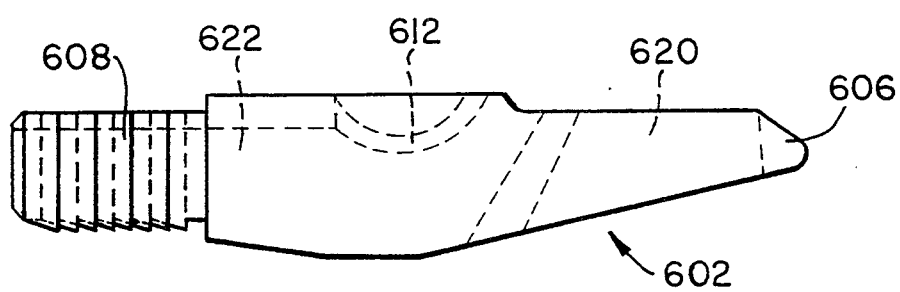
FIG. 5b is a side view of the stationary jaw of the punch of FIG. 3.

Turning to FIG. 5a and 5b, the stationary jaw 602 also has a shank portion 608 and a head portion 606. The shank portion 608 is similarly narrower than the head portion 606 and is provided with ribs 608a for engaging the interior of tube 15 (FIGS. 3a and 3b). The head portion 606 is provided with an opening 620 which receives the head portion 636 of the movable jaw 604 when in the closed position (FIG. 3b). Opening 620 is defined by walls 632 which engage the knife-like edge 616 of the movable jaw as the movable jaw is moved from the open to the closed position. Walls 632 narrow by tapered recess 630 which engages tapered shoulders 628 of the movable jaw 604. Between the head and shank portions of stationary jaw 602, there are provided arcuate flanges 612 which engage arcuate grooves 614 of the movable jaw 604. A throughbore or channel 622 (U-shaped or otherwise) extends through the shank portion 608 to the opening 620 for receiving push rod 60 as shown in FIGS. 3a and 3b.

As will be appreciated from the above description and from viewing FIGS. 3a and 3b, axial movement of the push rod 60 causes the jaws to open and close. Moreover, the weakest link in the operation of the jaws is the frangible link 60c, 60d of the push rod. Thus, when cutting hard bone tissue, should too much force be applied through the push rod, the frangible link will break before any portion of the end effector breaks, thereby preventing the accidental deposit of foreign material in the incised joint.

There has been described and illustrated herein an arthroscopic surgical instrument. While particular embodiments of the invention have been described, it is not intended that the invention be limited thereto, as it is intended that the invention be as broad in scope as the art will allow and that the specification be read likewise. Thus, while particular end effectors have been disclosed, it will be appreciated that other end effectors could be utilized with the frangible link concept of the invention. Moreover, while the surgical punch end effector is shown with the movable jaw having arcuate grooves and the stationary jaw having arcuate flanges, it will be appreciate that the flanges and grooves may be interchanged and the same results obtained. Also, while particular linkage means have been shown, it will be recognized that other types of linkage means could be used to couple the push rod with the end effector with similar results obtained. It will therefore be appreciated by those skilled in the art that yet other modifications could be made to the provided invention without deviating from its spirit and scope as so claimed.

What is claimed is:

1. An arthroscopic surgical instrument comprising:
   a) a hollow tube having a proximal and a distal end;
   b) end effector means of a first strength coupled to said distal end of said hollow tube;
   c) actuating means for actuating said end effector means, said actuating means coupled to said proximal end of said hollow tube;
   d) connector means for coupling said end effector means with said actuating means such that actuation of said actuating means results in movement of said end effector means, said connector means including a substantially cylindrical push rod having a flattened plate-like frangible link portion having at least two opposite flat substantially parallel surfaces, and coupling means of a second strength for coupling said push rod to said end effector means, wherein said frangible link has a third strength which is weaker than said first and second strengths, such that application of a force applied to said end effector means by said actuating means via said connector means causes said frangible link portion of said push rod to break prior to one of said end effector means and said coupling means breaking.

2. An arthroscopic surgical instrument according to claim 1, wherein:
   said flattened frangible link portion of said push rod includes a strength reducing throughbore.

3. A disposable arthroscopic surgical instrument according to claim 2, wherein:
   said end effector means comprises, a stationary jaw coupled to said distal end of said hollow tube, and a movable jaw coupled to said coupling means and pivotally coupled to said stationary jaw.

4. An arthroscopic surgical instrument according to claim 3, wherein:
   said stationary jaw is provided with a first arcuate engaging surface for engaging said movable jaw, and
   said movable jaw is provided with a second arcuate engaging surface for engaging said first arcuate engaging surface.

5. An arthroscopic surgical instrument according to claim 3, wherein:
   said stationary jaw is provided with a throughbore for receiving said connector means, and
   said coupling means comprises a pivot pin for coupling said movable jaw to said push rod.

6. An arthroscopic surgical instrument according to claim 3, wherein:
   said movable jaw is provided with a knife-sharp edge, and said stationary jaw is provided with an opening for receiving said movable jaw.

7. An arthroscopic surgical instrument according to claim 3, wherein:
   said first arcuate engaging surface comprises a pair of arcuate flanges, and said second arcuate engaging surface comprises a pair of arcuate grooves.

8. An arthroscopic surgical instrument according to claim 3, wherein:
   said push rod has a proximal end and a distal end and said distal end of said push rod is provided with a swaged flattened portion for coupling with said end effector means.

9. An arthroscopic surgical instrument according to claim 8, wherein:
   said swaged flattened portion is provided with a coupling throughbore for receiving said coupling means.

10. An arthroscopic surgical instrument according to claim 2, wherein:
    said push rod is composed of solution treated stainless steel hardened to a tensile strength of $-250,000/290,000$ psi.

11. An arthroscopic surgical instrument according to claim 10, wherein:
    said push rod has a diameter of $.061 \pm .001$ inches, said flattened portion has a thickness of $.030 \pm .002$ inches and a height of $.1 \pm .005$ inches, and said strength reducing throughbore has a diameter of $.076 \pm .001$ inches.

12. An arthroscopic surgical instrument, comprising:
    a) a hollow tube having a proximal and a distal end;
    b) actuating means coupled to said proximal end of said tube;
    c) a stationary jaw having a shank coupled to said distal end of said tube;
    d) a movable jaw pivotally coupled to said stationary jaw, wherein said stationary jaw has a first arcuate engaging surface comprises one of a flange and a groove for engaging said movable jaw, and said movable jaw has a second arcuate engaging surface comprises the other of said flange and said groove for engaging said first arcuate engaging surface; and e) connector means disposed inside said hollow tube for coupling said movable jaw with said actuating means such that movement of said actuating means results in movement of said movable jaw.

13. An arthroscopic surgical instrument according to claim 12, wherein:
said stationary jaw has a channel for receiving said connector means.

14. An arthroscopic surgical instrument according to claim 13, wherein:
said connector means comprises a push rod and a pivot pin coupled to said push rod, said pivot pin coupling said movable jaw to said push rod.

15. An arthroscopic surgical instrument according to claim 13, wherein:
said movable jaw is provided with a knife-sharp edge, and said stationary jaw is provided with an opening for receiving said movable jaw.

16. An arthroscopic surgical instrument according to claim 13, wherein:
said first arcuate engaging surface comprises a pair of arcuate flanges, and said second arcuate engaging surface comprises a pair of arcuate grooves.

17. An arthroscopic surgical instrument comprising:
a) a hollow tube having a proximal and a distal end;
b) end effector means of a first strength coupled to said distal end of said hollow tube, said end effector means comprising a stationary jaw coupled to said distal end of said tube, and a movable jaw pivotally coupled to said stationary jaw, wherein said stationary jaw has a first arcuate engaging surface for engaging said movable jaw, and said movable jaw has a second arcuate engaging surface for engaging said first arcuate engaging surface;
c) actuating means for actuating said end effector means, said actuating means coupled to said proximal end of said hollow tube;
d) connector means for coupling said end effector means with said actuating means such that actuation of said actuating means results in movement of said end effector means, said connector means including a substantially cylindrical push rod having a flattened frangible link portion having a strength reducing throughbore therein, and coupling means of a second strength for coupling said push rod to said end effector means, wherein said frangible link has a third strength which is weaker then said first and second strengths, such that application of a force applied to said end effector means by said actuating means via said connector means causes said frangible link portion of said push rod to break prior to one of said end effector means and said coupling means breaking.

18. An arthroscopic surgical instrument according to claim 17, wherein:
said stationary jaw is provided with a throughbore for receiving said connector means,
said coupling means comprises a pivot pin for coupling said movable jaw to said push rod,
said movable jaw is provided with a knife-sharp edge,
said stationary jaw is provided with an opening for receiving said movable jaw, and
said first arcuate engaging surface comprises a pair of arcuate flanges, and said second arcuate engaging surface comprises a pair of arcuate grooves.

19. An arthroscopic surgical instrument according to claim 17, wherein:
said push rod is composed of solution treated stainless steel hardened to a tensile strength of −250,000/290,000 psi.

20. An arthroscopic surgical instrument according to claim 19, wherein:
said push rod has a diameter of .061±.001 inches, said flattened portion has a thickness of .030±.002 inches and a height of .1±.005 inches, and said strength reducing throughbore has a diameter of .076±.001 inches.

* * * * *